United States Patent [19]
Kovacs et al.

[11] Patent Number: 6,051,422
[45] Date of Patent: Apr. 18, 2000

[54] HYBRID BIOSENSORS

[75] Inventors: Gregory T. A. Kovacs, Stanford; David A. Borkholder, San Jose, both of Calif.

[73] Assignee: Board of Trustees, Leland Stanford, Jr., University, Stanford, Calif.

[21] Appl. No.: 09/113,015

[22] Filed: Jul. 9, 1998

Related U.S. Application Data

[62] Division of application No. 08/866,063, May 30, 1997.

[51] Int. Cl.$^7$ .................................................. C12M 3/00
[52] U.S. Cl. ................................. 435/287.1; 435/288.7; 204/403; 324/446; 324/692
[58] Field of Search .............................. 435/173.1, 173.4, 435/285.2, 287.1, 288.7; 204/403; 356/246, 446; 324/447, 692

[56] References Cited

U.S. PATENT DOCUMENTS

| | | |
|---|---|---|
| 3,890,201 | 6/1975 | Cady . |
| 4,054,646 | 10/1977 | Giaever . |
| 4,072,576 | 2/1978 | Arwin et al. . |
| 4,072,578 | 2/1978 | Cady et al. ............................. 195/127 |
| 4,151,049 | 4/1979 | Janata ..................................... 204/1 T |
| 4,156,180 | 5/1979 | Annen et al. ........................ 324/57 R |
| 4,160,205 | 7/1979 | Hobbs et al. . |
| 4,200,493 | 4/1980 | Wilkins et al. . |
| 4,264,728 | 4/1981 | Wilkins ....................................... 435/5 |
| 4,335,206 | 6/1982 | Wilkins et al. ........................... 435/34 |
| 4,368,423 | 1/1983 | Liburdy ................................ 324/65 R |
| 4,472,506 | 9/1984 | Liburdy ..................................... 436/63 |
| 4,490,216 | 12/1984 | McConnell ............................... 204/1 T |
| 4,920,047 | 4/1990 | Giaever et al. . |
| 5,187,096 | 2/1993 | Giaever et al. . |
| 5,314,495 | 5/1994 | Kovacs ..................................... 623/25 |
| 5,432,086 | 7/1995 | Franzl et al. ............................ 435/291 |
| 5,563,067 | 10/1996 | Sugihara et al. ..................... 435/287.1 |

OTHER PUBLICATIONS

Biosensors & Bioelectronics 6, pp. 359–367, 1991.
C. Lo, et al., pH Changes in Pulsed $CO_2$ Incubators Cause Periodic Changes in Cell Morphology, Academic Press, Inc. 1994.
C. Lo, et al., Impedance Analysis of MDCK Cells Measured by Electric Cell–Substrate Impedance Sensing, Biophysical Society, 1995.
I. Giaever, et al., A morphological biosensor for mammalian cells, Nature, vol. 366, Dec. 9, 1993.
I. Giaever, et al., Use of Electric Fields to Monitor the Dynamical Aspect of Cell Behavior in Tissue Culture, IEEE Transactions on Biomedical Engineering, vol. BME–33, No. 2, Feb. 1986.
D. A. Borkholder, et al., Impedance Imaging for Hybrid Biosensor Applications, Solid–State Sensor and Actuator Workshop Hilton Head, South Carolina, Jun. 2–6, 1996, pp. 156–160.

(List continued on next page.)

*Primary Examiner*—David A. Redding
*Attorney, Agent, or Firm*—Coudert Brothers

[57] ABSTRACT

The invention relates to an apparatus and method for monitoring cells and to a method for monitoring changes in cells upon addition of an analyte to the cell's environment, comprising a device which includes an array of microelectrodes disposed in a cell culture chamber, upon which array a portion of cells adhere to the surfaces of the microelectrodes. The diameter of the cells are larger than the diameters of the microelectrodes. A voltage signal is applied across each of the microelectrodes and a reference electrode. Detection and monitoring of the signals resulting from the application of the voltage signal provides information regarding the electrical characteristics of the individual cells, including impedance (combined cell membrane capacitance and conductance), action potential parameters, cell membrane capacitance, cell membrane conductance, and cell/substrate seal resistance. Such an invention is useful in detecting or screening a variety of biological and chemical agents.

30 Claims, 8 Drawing Sheets

OTHER PUBLICATIONS

P. M. Ghosh, et al., Morphological response of mammalian cells to pulsed ac fields, Bioelectrochemistry and Bioenergetics, 33 (1994) pp. 121–133.

I. Giaever, et al., Toxic? Cells can tell, Chemtech, Feb. 1992, pp. 116–125.

C. R. Keese, et al., A Whole Cell Biosensor Based On Cell–Substrate Interactions, Annual Int'l Conf. Of the IEEE Engineering in Medicine and Biology Society, vol. 12, No. 2, 1990.

P. Connolly, et al., Extracelluar electrodes for monitoring cell cultures, 1989 IOP Publishing Ltd., pp. 39–50.

C.R. Keese, et al., A Biosensor That Monitors Cell Morphology With Electrical Fields, IEEE Engineering In Medicine and Biology, Jun./Jul. 1994.

P. M. Ghosh, et al., Monitoring electropermeabilization in the plasma membrane of adherent mammalian cells, Biophys. J. Biophysical Society, vol. 64, May 1993, pp. 1602–1609.

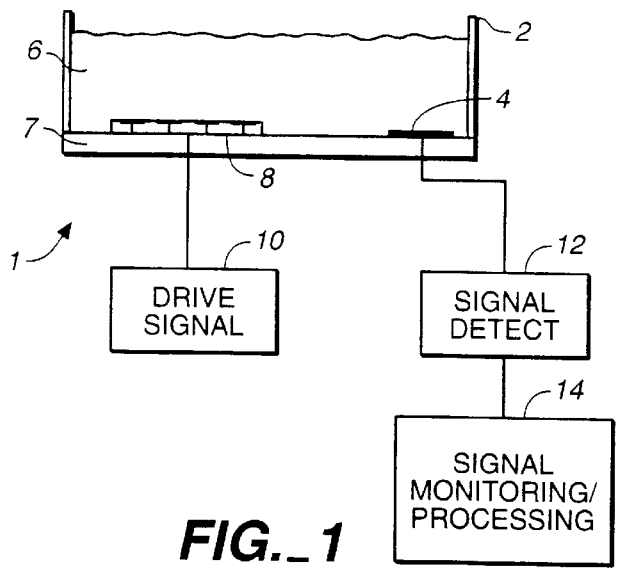
FIG._1
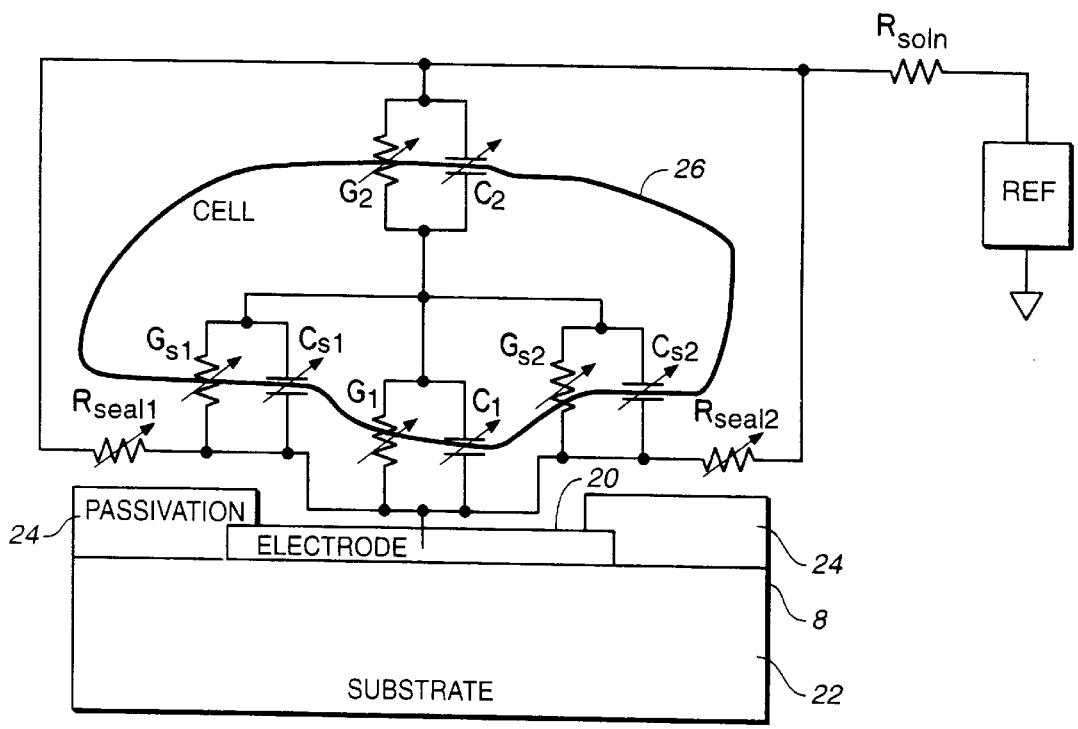
FIG._2B

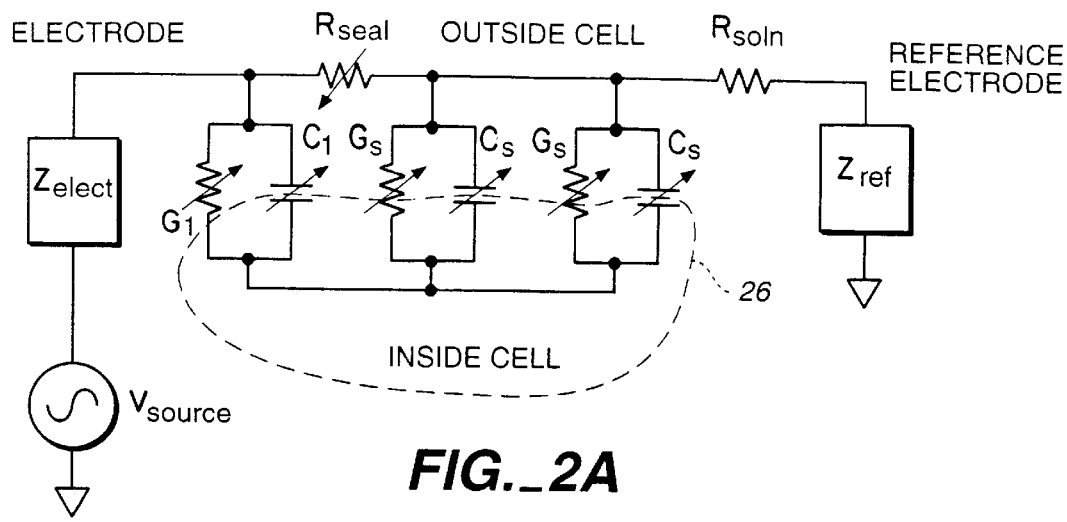
FIG._2A
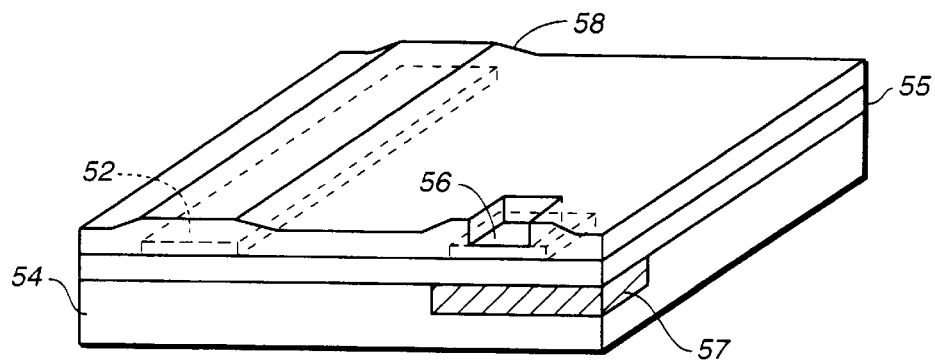
FIG._5
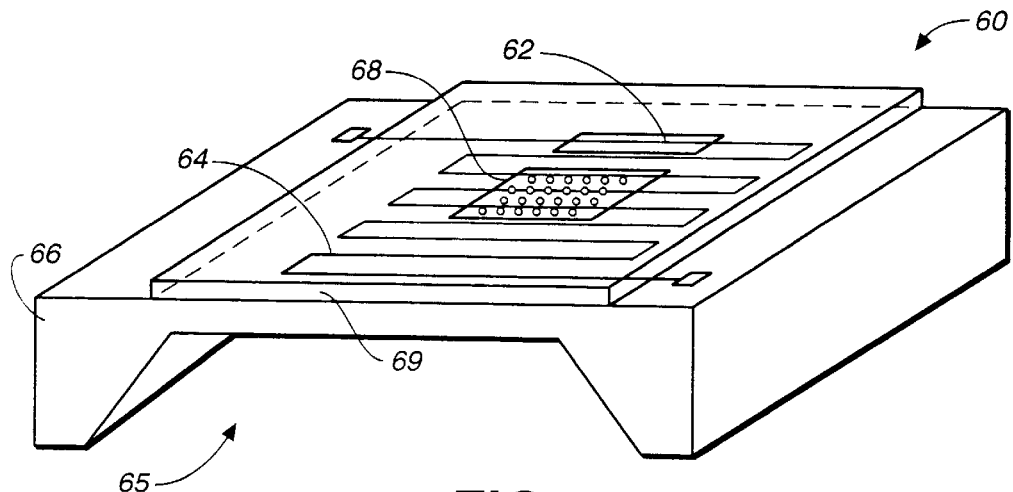
FIG._6

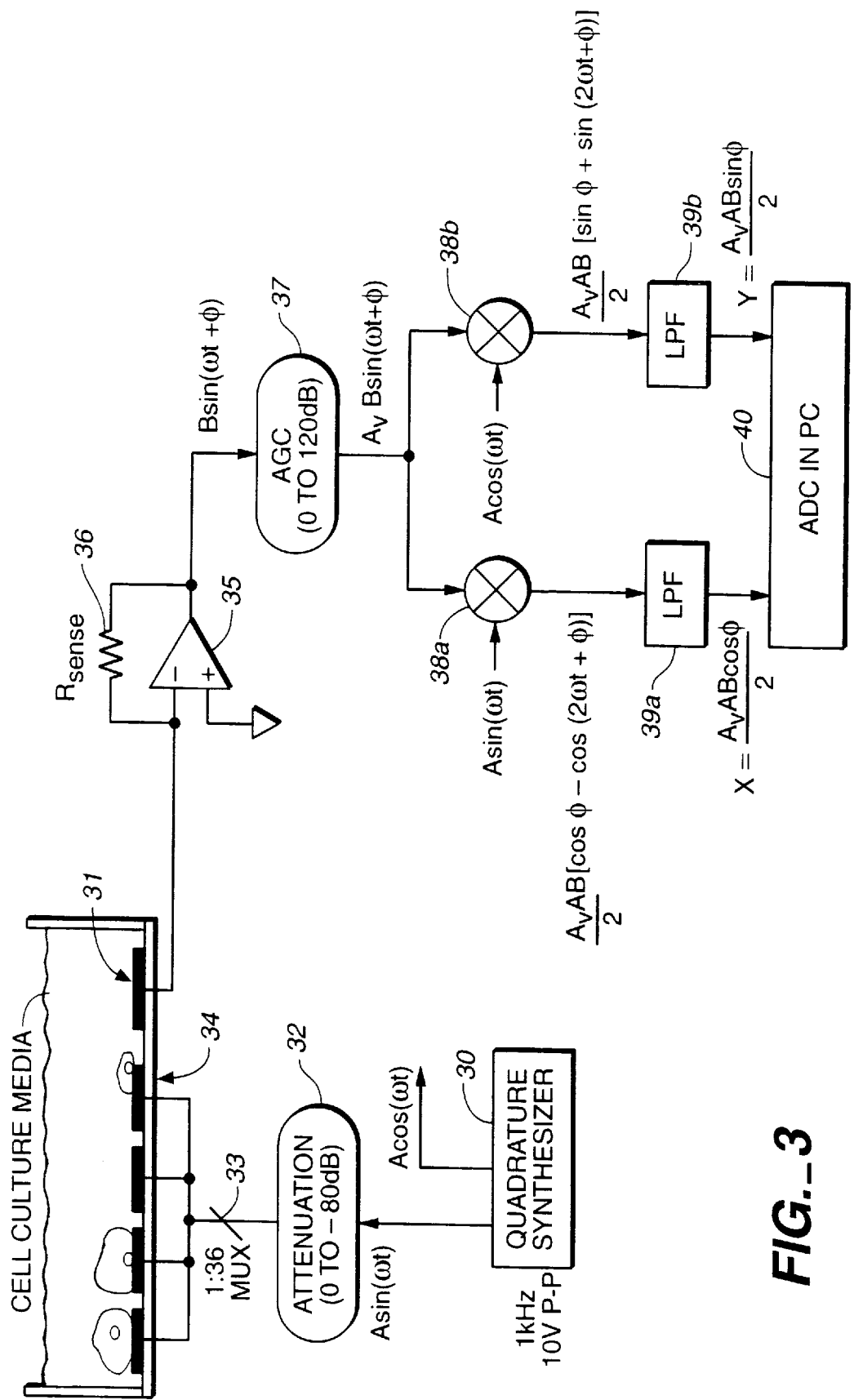
FIG._3

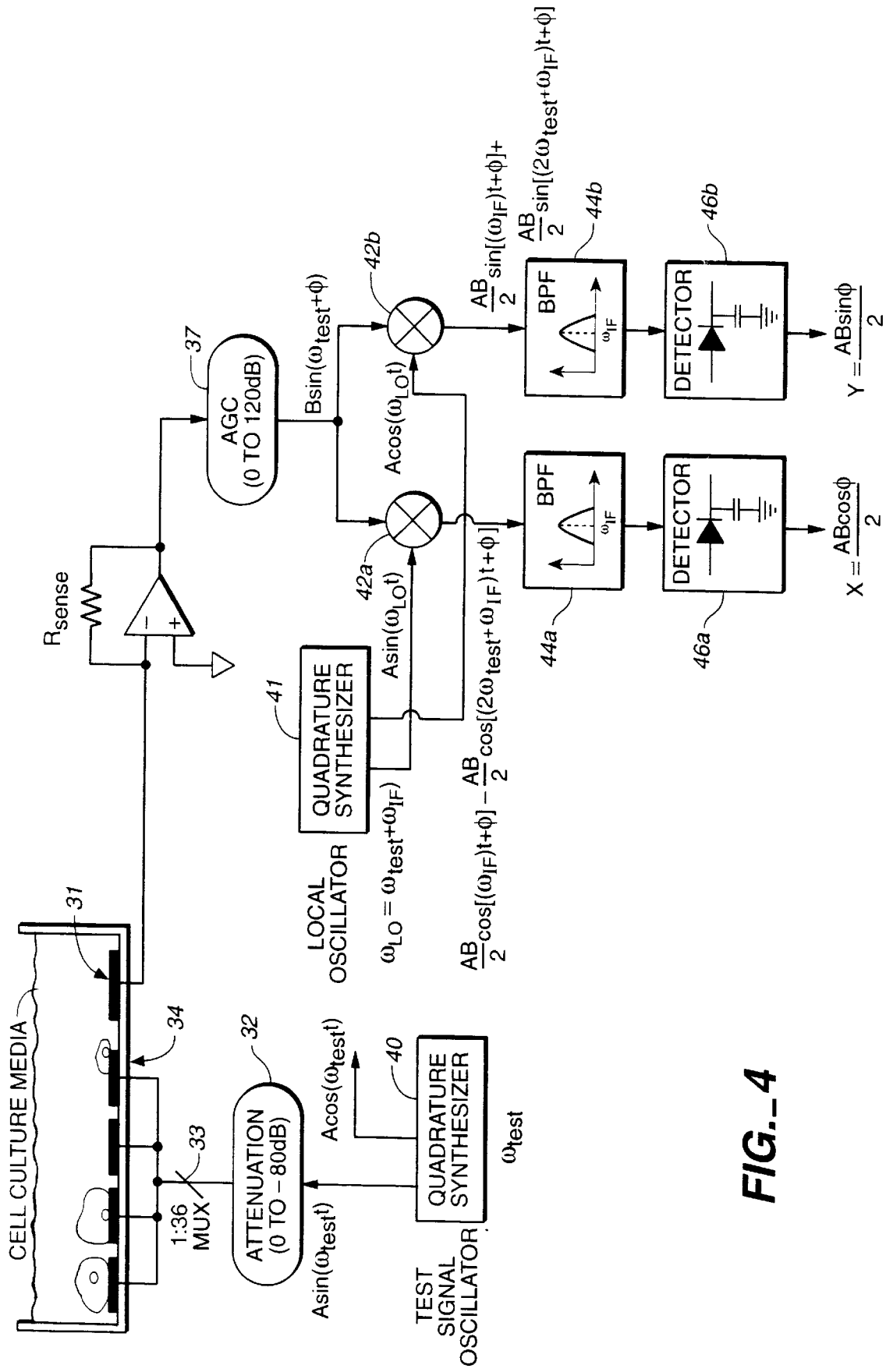
FIG._4

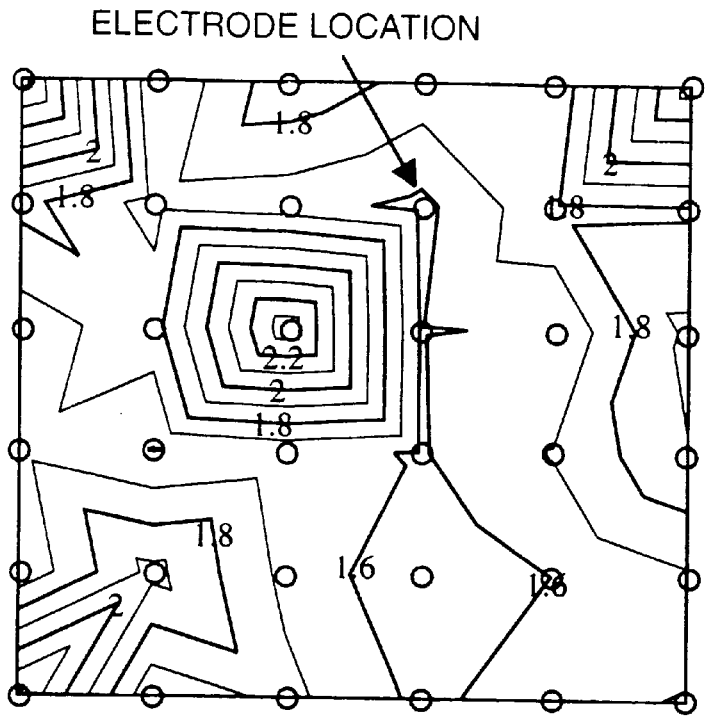
FIG._7B
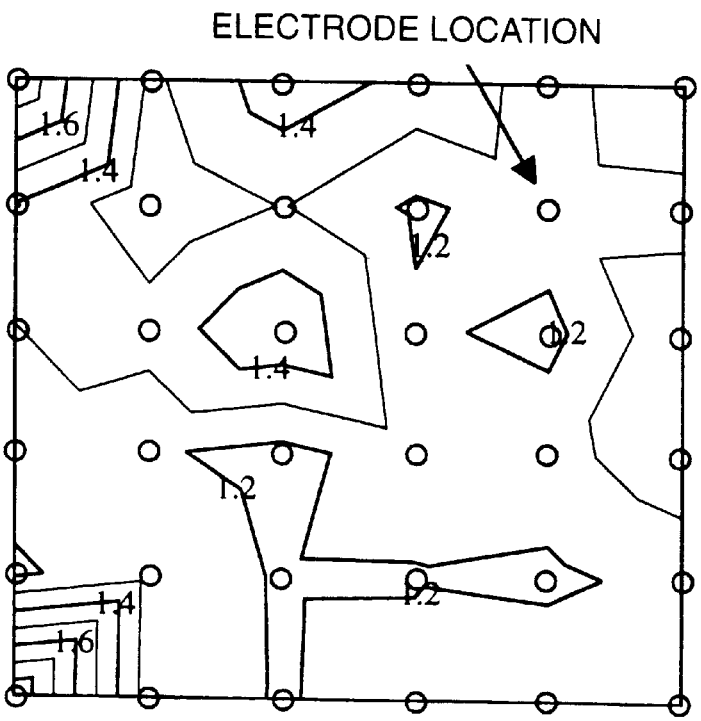
FIG._8B

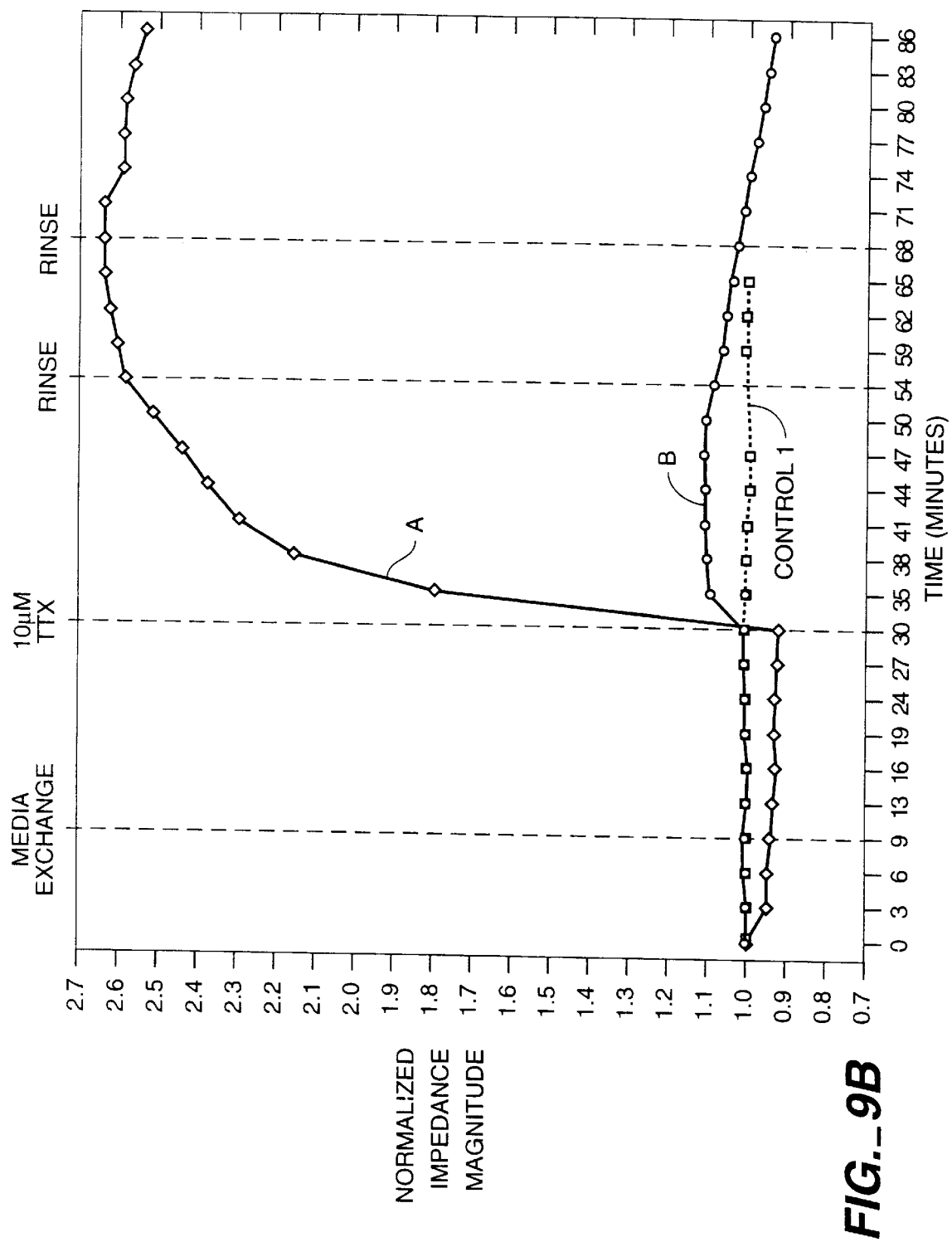
FIG._9B

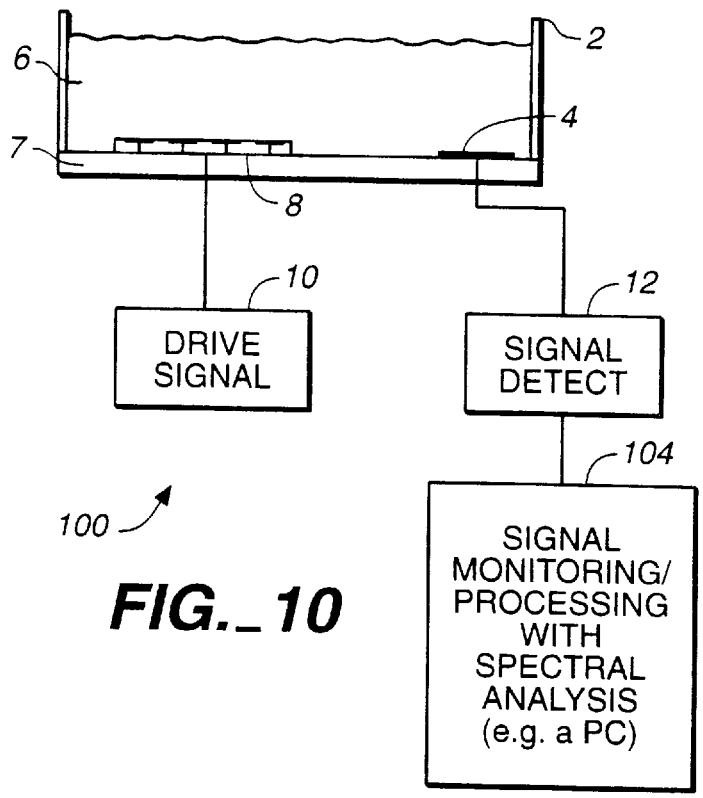
FIG._10
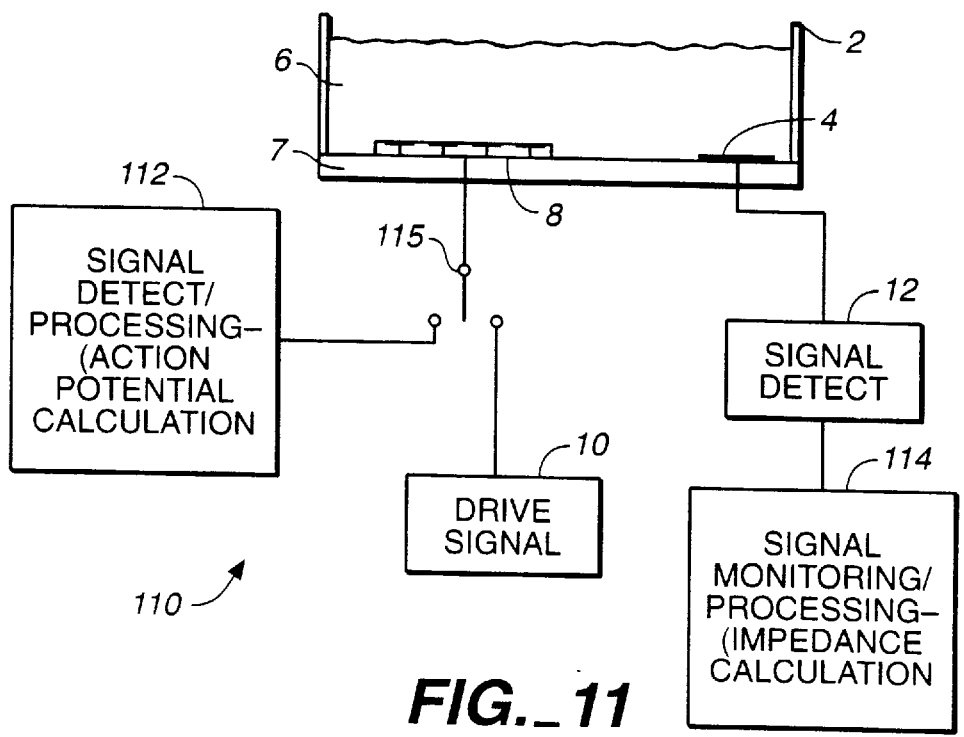
FIG._11

HYBRID BIOSENSORS

This application is a div. of Ser. No. 08/866,063 filed May 30, 1997.

This invention was made with Government support under contract N66001-96-C-8631 awarded by the Defense Advanced Research Projects Agency. The Government has certain rights in this invention.

BACKGROUND OF THE INVENTION

1. Field of the Invention

This invention relates to an apparatus and method for monitoring cells which have been cultured onto electrodes of a microfabricated array. More particularly, it relates to an apparatus and method for monitoring various characteristics of such cells, such as cellular health, cellular adhesion to an electrode or substrate, and changes in cellular impedance, action potential parameters, membrane capacitance, membrane conductance, and cell/substrate seal resistance. It also relates to a technique for evaluating the effect of an analyte (which analyte can include pharmaceutical agents and toxins) upon a cell, and a technique for quality control testing of wet electrochemical systems which utilize microelectrodes.

2. Description of Related Art

Biosensors—sensors including biological materials employed to detect and/or monitor an environment—offer several advantages. Biosensor development can utilize the highly sensitive nature of biological materials to detect directly the presence or absence of analytes by their affect upon cellular metabolism. Thus, for example, utilizing cultured cell systems it is possible to screen for a broad range of toxins, achieving a fast response time, while maintaining high sensitivity. Moreover, a degree of selectively may be achieved by choice of cell type.

Cellular metabolism refers to the orchestration of the chemical and enzymatic reactions that constitute the life process of a cell. These reactions include a vast number of different chemical and enzymatic reactions, relating to the growth and maintenance of the cell. Contemplation of the wide variety of functions that a cell carries out—DNA replication, DNA transcription, RNA translation, digestion of macromolecules, construction of macromolecules, and monitoring of the extracellular and intracellular milieus—provides one with a profound appreciation of the complexity of cellular metabolism. These chemical and enzymatic reactions occur simultaneously within an active cell. Moreover, these reactions do not take place in isolation; rather the pace of each reaction is regulated, in turn, by the product of one or more other reactions. Overall, the organization of cellular metabolism is embedded in a vast network of inter-related cellular reactions. Given this interdependency, it is apparent that analytes that affect one or more aspects of cellular metabolism are likely to manifest their impact on characteristics of the cell, including impedance; action potential parameters, including action potential rate, action potential amplitude, and action potential shape, among others; membrane conductance, and membrane capacitance.

Because of the above advantages, biosensors including live, intact cells (referred to as hybrid biosensors) have several commercially significant applications. For example, such biosensors are particularly useful in detecting chemical and biological warfare (CBW) agents. Biosensors may also supplement existing methods for pharmaceutical screening. It is possible that this type of biosensor technology will eliminate, or at least greatly reduce, animal testing employed in pharmaceutical screening.

Some progress in the development of hybrid biosensor technology has been described within the scientific literature. For example, techniques have been described by Giaever and Keese (in conjunction with others) to monitor the impedance characteristics at cell/electrode interfaces. See M. Kowolenko et al., "Measurement of Macrophage Adherence and Spreading with Weak Electric Fields," *Journal of Immunological Methods*, 127, 71–77 (1990); C. R. Keese et al., "A Whole Cell Biosensor Based on Cell-Substrate Interactions," *Annual International Conference of the IEEE Engineering in Medicine and Biology Society*, Vol. 12, No. 2, (1990); P. M. Ghosh et al., "Monitoring Electropermeabilization in the Plasma Membrane of Adherent Mammalian Cells," *Biophys. Journal*, 64, 1602–09 (1993); C. R. Keese et al., "A Biosensor that Monitors Cell Morphology with Electrical Fields," *IEEE Engineering in Medicine and Biology*, June/July 1994, 402–08; I. Giaever et al., "Use of Electric Fields to Monitor the Dynamical Aspect of Cell Behavior in Tissue Culture," *IEEE Transactions on Biomedical Engineering*, Vol. BME-33, No.2, February 1986; U.S. Pat. No. 4,054,646; U.S. Pat. No. 4,920,047; and U.S. Pat. No. 5,187,096. However, the systems described by Giaever and Keese utilize large area (e.g., 250 µm diameter) electrodes which cannot be completely covered by a single cell. Therefore, accurate measurement of an individual cell's impedance characteristics is interfered with by the parallel impedance of the uncovered electrode area and the impedance of cell-cell contact areas (due to the space between adjacent cells). Moreover, the efforts of Giaever and Keese reveal only motility changes in cells. Further, cellular membranes are modeled as having a constant capacitance and conductance; any changes in capacitance and conductance are explained in terms of varying cellular membrane area.

In Lind et al., "Single Cell Mobility and Adhesion Monitoring Using Extracellular Electrodes" *Biosensors and Bioelectronics*, 6, 359–67 (1991), a system using relatively large area electrodes similar to that described above was employed, as well as a system utilizing electrodes smaller than the cell to be monitored. In this system, single cell effects could be examined without the shunting effects described above, but this system was only used to monitor cell motility by means of changes in the impedance. Moreover, in such systems membrane conductance and capacitance was presumed to be constant.

Accordingly, there remains a need for a technique that utilizes electrodes smaller than a cell's diameter, but which provides for monitoring changes in cellular membrane capacitance and conductance. Such a technique would also permit monitoring of activation of voltage-gated ionic channel conductance. In addition, such a technique would permit detection and monitoring of compounds that affect the impedance, action potential parameters, membrane conductance, membrane capacitance of a cell, and cell/substrate seal resistance.

Voltage-gated $Na^+$ channels (among other ion channels) help make nerve cells electrically excitable and enable them to conduct action potentials. When the membrane of a cell with many $Na^+$ channels is partially depolarized by a momentary stimulus, some of the channels promptly open, allowing $Na^+$ ions to enter the cell. The influx of positive charge depolarizes the membrane further, thereby opening more channels, which admit more $Na^+$, causing still further depolarization. This process continues in a self-amplifying fashion until the membrane potential has shifted from its resting value of about −70 mV all the way to the $Na^+$ equilibrium potential of about +50 mV. At that point, where the net electrochemical driving force for the flow of $Na^+$ is zero, the cell would come to a new resting state with all its Na$^+$ channels permanently open, if the open channel conformation were stable. The cell is saved from such a permanent electrical spasm by the automatic inactivation of the Na$^+$ channels, which now gradually close and stay closed until the membrane potential has returned to its initial negative resting value. The whole cycle, from initial stimulus to return to the original resting state, takes a few milliseconds or less.

In many types of neurons, though not all, the recovery is hastened by the presence of voltage-gated K$^+$ channels in the plasma membrane. Like the Na$^+$ channels, these channels open in response to membrane depolarization, but they do so relatively slowly. By increasing the permeability of the membrane to K$^+$ just as the Na$^+$ channels are closing through inactivation, the K$^+$ channels help to bring the membrane rapidly back toward the K$^+$ equilibrium potential, so returning it to the resting state. The repolarization of the membrane causes the K$^+$ channels to close again and allows the Na$^+$ channels to recover from their inactivation. In this way the cell membrane can be made ready in less than a millisecond to respond to a second depolarizing stimulus.

Examining the membrane potential relative to time, an action potential exhibits various characteristics or parameters, including action potential rate (if cells spontaneously depolarize), action potential amplitude, and action potential shape, among others. Action potential rate refers to the frequency with which a cell produces an action potential (rapid depolarization). Action potential amplitude refers to the height of the peak depolarization that occurs in the course of the action potential. Action potential shape refers to the time course of the depolarization and repolarization.

There is also a need in the art for an apparatus for monitoring cells employing an electrode array having reduced electrode diameter and low electrode impedance, thus allowing for detection and monitoring of changes in the cellular membrane of an individual cell.

These results, among others, had not been achieved in the prior art.

SUMMARY OF THE INVENTION

Accordingly, an object of the present invention is to provide an apparatus and method for monitoring cells, which apparatus and method are characterized by a resolution sufficient to monitor the impedance, action potential parameters, cellular membrane capacitance, cellular membrane conductance, and cell/substrate seal resistance of individual cells, and changes therein. The invention further allows measurements to be made across a large number of microelectrodes at numerous frequencies and excitation voltages.

Another object of the present invention is to provide an apparatus and method for monitoring cells, which apparatus and method are capable of monitoring the impedance, and changes therein, of individual cells and has an integral pH sensor, for monitoring the extracellular fluids.

Still another object of the present invention is to provide an apparatus and method for monitoring cells, which apparatus and method are capable of monitoring the impedance of individual cells, and changes therein, and having an integral heater and, optionally, a thermal isolation membrane, for maintaining the cells and the array at a desired temperature.

Yet another object of the present invention is to provide an apparatus and method for monitoring cells, which apparatus and method are capable of monitoring the impedance of individual cells, and changes therein, and having an integral temperature sensor for closed loop thermal regulation.

Another object of the present invention is to provide an apparatus and method for monitoring cells, which apparatus and method are capable of monitoring the impedance and action potential parameters of individual cells, and changes therein, simultaneously.

Still another object of the present invention is to provide an apparatus and method for monitoring cells, which apparatus and method are capable of activating a voltage-gated ion channel, while detecting the impedance of individual cells, and changes therein.

Another object of the present invention is to provide an apparatus and method for monitoring cells, which apparatus and method are capable of monitoring the impedance and action potential parameters of individual cells, and changes therein, using totipotent primordial cells (immortal cells which can be differentiated into any normal tissue type), or any cell type differentiated from a totipotent cell.

Still another object of the present invention is to provide an apparatus and method for monitoring cells, which apparatus and method are capable of detecting and/or measuring the action of a pharmaceutical agent, drug, environmental factor, toxin, chemical agent, biological agent, or virus by monitoring the impedance and/or action potential parameters of individual cells, and changes therein.

Another object of the present invention is to provide an apparatus and method for monitoring cells, which apparatus and method are capable of monitoring the impedance and/or action potential parameters of individual cells, and changes therein, employing high frequency heterodyning to determine the time course of the impedance and the action potential parameters.

It is yet another object of the invention to provide an apparatus and method for monitoring cells, which apparatus and method are capable of detecting and monitoring the cellular membrane conductance and cellular membrane capacitance of individual cells, and changes therein.

It is still another object of the invention to provide an apparatus and method for monitoring cells, which apparatus and method are capable of determining the location or position of cells well-coupled to the substrate/electrode.

It is another object of the invention to provide an apparatus and method for monitoring cells, which apparatus and method are capable of measuring the degree to which cultured cells adhere to the respective surfaces of particular microelectrodes and of assessing the effectiveness of a cellular adhesion promoter (including, by not limited to Self-Assembled Monolayers), by means of detecting and monitoring the impedance of individual cells, and changes therein.

Still another object of the present invention is to provide an apparatus and method for monitoring cells capable of monitoring the impedance and/or action potential parameters of individual cells, and changes therein, employing spectral analysis to monitor changes in the impedance and/or action potential of individual cells.

These objects, among others, have been achieved by means of an apparatus for monitoring cells, comprising a monolithic device which includes an array of microelectrodes disposed over a substrate, with each member of the array of microelectrodes being individually connected via conductive traces to contact points ("bond pads") for electrical connection of external circuits. The integrated device is disposed in a cell culture chamber, which chamber is configured to contain a medium for cultured cells in a volume surrounding the respective surfaces of the microelectrodes. Cells are introduced into the cell culture chamber and a portion of the cells adhere to the surface of the microelectrodes, wherein the diameter of a cell is larger than the diameter of a microelectrode. An electrical signal is selectively applied between each of the microelectrodes and a large reference electrode, which is disposed within the cell culture chamber, and the signals resulting from the application of the signal are detected. Using the detected signals, various electrical characteristics of the microelectrode and cell junctions are monitored. According to one preferred embodiment, the apparatus monitors impedances between each microelectrode and the reference electrode. Using the impedance values, a variety of characteristics of individual cells which adhere to the microelectrodes can be monitored, such as cell membrane capacitance, cell membrane conductance, action potential parameters, and cell/substrate seal resistance.

These objects, among others, have also been achieved by means of a method of monitoring cells comprising the steps of providing in a cell culture chamber a monolithic device that includes an array of planar microelectrodes disposed on a substrate, wherein the diameter of a cell is larger than the diameter of a microelectrode, the array of microelectrodes being connected to a conductive pattern having contacts points connected thereto; culturing cells in a medium provided within the cell culture; incubating the cells; selectively applying an electrical signal between each microelectrode and a reference electrode disposed within the medium; detecting signals resulting from the application of the signal across the microelectrodes and the reference electrode; monitoring characteristics of individual cells which adhere to the respective surfaces of the microelectrodes based on impedance values derived from the resulting signals, the characteristics being selected from the group consisting of impedance, action potential parameters (e.g., rate, amplitude, shape, etc.), cell membrane capacitance, cell membrane conductance, and cell/substrate seal resistance.

These objects, among others, have also been achieved by means of a method of monitoring the effect of an analyte in vitro comprising the steps of providing in a cell culture chamber a monolithic device that includes an array of planar microelectrodes disposed on a substrate, the array of microelectrodes being connected to a conductive pattern having contacts points connected thereto; culturing cells in a medium provided within the cell culture chamber, wherein the diameter of a cell is larger than the diameter of a microelectrode; incubating the cells; selectively applying an electrical signal between each microelectrode and a reference electrode disposed within the medium; detecting signals resulting from the application of the signal between the microelectrodes and the reference electrode; determining characteristics of individual cells which adhere to the respective surfaces of the microelectrodes, the characteristics being selected from the group consisting of impedance, action potential parameters, cell membrane capacitance, cell membrane conductance, and cell/substrate seal resistance; introducing the analyte into the medium; repeating the step of determining; and comparing the characteristics both prior to and subsequent to introducing the analyte and monitoring the effect of the analyte on the cells which adhere to the microelectrodes.

According to other aspects of the invention, the device comprises a monolithic structure which contains one or a combination of several integral components. In one embodiment, the monolithic device includes a sensor which provides an electrical signal indicative of the pH of the medium. In another embodiment, the integrated device includes a heating means, such as a thin film heater, and may contain a thermal isolation means. In an alternate embodiment, the integrated device further includes a temperature sensor which is used to selectively activate a heater means, thereby regulating the temperature. In other preferred embodiments, the integrated device includes any combination of such components.

According to yet another aspect of the invention, the invention is used for quality control testing of wet electrochemical systems which utilize microelectrodes.

According to another aspect of the invention, the invention is used to monitor the effectiveness of an adhesion promoting agent.

Other aspects, features and advantages of the present invention will be apparent from the detailed description of the invention set forth below.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 presents a generalized block diagram of a system in accordance with the present invention;

FIGS. 2A and 2B are diagrams of equivalent circuits between each microelectrode and a reference electrode;

FIG. 3 is a block diagram of a system according to a first embodiment of the invention in which signals are detected using a homodyne technique;

FIG. 4 is a block diagram of a system according to a second embodiment of the invention in which signals are detected using a heterodyne technique;

FIG. 5 is a cross-sectional view of a portion of a monolithic structure that includes an array of microelectrodes according to an embodiment of the invention;

FIG. 6 is a cross-sectional view of a monolithic, integrated structure including an array of microelectrodes according to an alternate embodiment of the invention;

FIG. 7B is a two-dimensional impedance magnitude map of the electrode array shown in FIG. 7A, normalized to the bare chip impedance;

FIG. 8B is a two-dimensional image magnitude map of the electrode array shown in FIG. 8A, normalized to the bare chip impedance.

FIG. 9B is a graph of the normalized impedance magnitude of electrodes A, B, and the electrode labeled Control 1 in FIG. 9A.

FIG. 10 is a block diagram of a system according to an alternate embodiment of the invention in which processing means are provided which perform real time spectral analysis.

FIG. 11 is a block diagram of a system according to an alternate embodiment of the invention for measuring action potential parameters substantially simultaneously with measuring impedance.

DESCRIPTION OF THE PREFERRED EMBODIMENTS

Figure 7A:
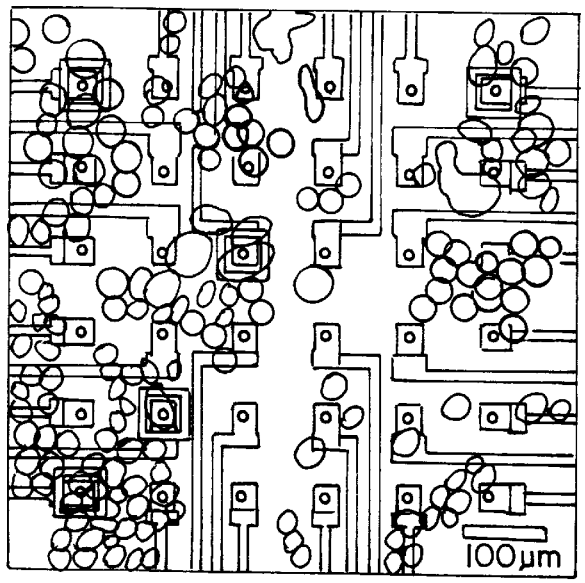
FIG. 7A is a diagramatic represention of an optical photograph of NG108-15 cells growing on an electrode array, according to one example of the invention.

Referring now to the drawings, wherein like reference numbers designate identical or corresponding parts throughout the several views, and more particularly to FIG. 1 thereof, which is a generalized block diagram of a system 1 according to the present invention. The system 1 includes a chamber 2, which may be used to culture cells. A monolithic structure is provided within the area defined by the chamber 2. For example, a standard Petri dish or equivalent structure is bonded to the monolithic structure to define a cell culture chamber. As described in greater detail below in reference to FIGS. 5 and 6, the monolithic structure includes an array of planar microelectrodes 8 disposed on a substrate 7. Each of the microelectrodes are connected electrically to a contact point connected to a signal generation means 10. The signal generation means 10 selectively drives each of the microelectrodes with an electrical signal. The electrical signal can be either a voltage signal or a current signal. The resulting signals are detected at the reference electrode 4 by signal detection means 12. These elements, described more particularly in reference to FIGS. 3 and 4, are characterized by high noise immunity. Preferably, solid state integrated circuit components are utilized. The detected signal is processed with monitoring and processing means 14 in order to measure the impedances between each microelectrode and the reference electrode 4. These measurements can be made before, after, or during incubation of cells in the chamber 2.

In a preferred embodiment of the invention, cells are cultured within the medium 6 according to known techniques. A layer of cells (not shown) adhere to the respective surfaces of the microelectrode array 8 provided on the integrated device. As each of the microelectrodes is driven with the applied voltage signal, a current flows between the microelectrodes and the reference electrode. The impedance is determined from this current signal. Based on the impedance, various electrical characteristics of the cells which adhere to the surfaces of the microelectrodes can be monitored. Such characteristics include the impedance of the individual cell (i.e., the combined cell membrane capacitance and conductance), the action potential parameters of the individual cell, the cell membrane capacitance, the cell membrane conductance, and the cell/substrate seal resistance. The action potential parameters include, among others, action potential rate, action potential amplitude, and action potential shape and action potential power spectrum. These action potential parameters are determined by means of impedance measurements. This is accomplished, for example, by noting changes in a cell's membrane conductance.

It is a feature of the invention that each of the microelectrodes is sufficiently small to enable monitoring of an individual cell and its cellular membrane. Conventionally, the relative size of the reference electrode is large in comparison to the measuring electrodes so that the measured impedance across each electrode and the reference electrode is dominated by the interface between the microelectrode and the cell and the cell membrane impedance. In addition, the present invention utilizes microelectrodes with a small surface such that the diameter of a cell is larger than the diameter of a microelectrode so that electrical characteristics related to individual cells and cell membranes can be resolved. The specific size of the microelectrodes will vary according to the specific application and size of the cells to be monitored. Preferably, the diameter of the microelectrodes is less then or equal to one-half the diameter of the cell to be monitored, thereby permitting a given microelectrode to monitor an individual cell and cell membrane. For example, in one preferred embodiment, microelectrodes with diameters of about 4 to 20 $\mu$m have been utilized. The combination of the relatively small size of the microelectrodes, the relatively low impedance of the microelectrodes (i.e., relative to cell membrane impedance) and the low noise characteristics of the signal detection components 12 enables the present invention to monitor changes in the electrical characteristics of the cell, including changes in the capacitance and conductance of the cellular membrane. It also permits a variety of other techniques, described in greater detail below. These techniques include monitoring the action potential parameters of the cells; monitoring activation of voltage-gated ion channels; pharmaceutical screening and toxin detection; identifying particular cell/microelectrode junctions characterized by a higher degree of cell adherence to the microelectrode, and testing changes in cell adherence as adhesion promoting agents are employed.

It will be understood that the signal monitoring and processing means referred to in FIG. 1 may comprise various devices for calculating the various cellular characteristics referred to above. For example, this element may comprise a personal computer configured to calculate the impedance between each microelectrode and the reference electrode 4 based on the signals detected with the signal detecting means 12. By monitoring these values over time, the present invention can determine the various characteristics of individual cells which adhere to each microelectrode. As described below in reference to FIG. 10, the signal monitoring and processing means may be configured to perform a spectral analysis so as to monitor, in real time, characteristics such as changes in cell action potential parameters and cell impedance.

FIGS. 2A and 2B are diagrams of equivalent circuits for the circuit established between each microelectrode and the reference electrode. Referring to FIG. 2B, a single cell is disposed over the surface of a microelectrode 20 on a chip 8. While many cells will adhere to the chip, a single cell is shown for the purpose of this discussion. It will be appreciated that it is possible that more than one cell could be over a single microelectrode. The surface of a single microelectrode 20 of the array is exposed through a via in a passivation layer 24 provided over a substrate 22. The microelectrode is driven with a signal source relative to the reference electrode 4.

The microelectrode 20 has a known impedance $Z_{elect}$ (shown in FIG. 2A). As known in the art, this value is described by a classical model of a metal in an electrolyte, and is calculated based on the material of the microelectrode or is measured separately prior to introduction of cells into the system. In series with the impedance of the microelectrode is the resistance of the solution $R_{soln}$ and the respective capacitance and conductive values associated with the microelectrode/cell junction. Parasitics to the substrate and parasitics to the passivation layer 24 (from the electrolyte) are not shown. The former may be reduced by use of a glass substrate, or may be factored out by normalizing.

Although often modeled as constants in prior art systems, the values of the capacitance and conductance associated with the cell 26 actually vary in response to added toxins, pharmaceuticals and other substances, applied voltages, and changes in cellular morphology. In the example shown, $C_1$ and $G_1$ identify the respective capacitance and conductance values of the cell membrane disposed directly over the microelectrode 20. $C_2$ and $G_2$ are the capacitance and conductance, respectively, of the top surface of the membrane in contact with the solution. $C_S$ and $G_S$ refer to the respective capacitance and conductance of the cell membrane disposed over the passivation layer 24. The seal resistance of the cell, $R_{seal}$, is a resistance which also varies; this value depends on the cell-substrate separation and the distance from the exterior edge of the electrode to the outside of the cell. The intracellular solution resistance is insignificant with respect to the membrane impedance and may be ignored.

It is noted that FIG. 2A generally refers to the sum of the respective resistance and conductance values which comprise the total seal resistance $R_{seal}$. The two-dimensional, cross-sectional view of FIG. 2B illustrates components of this resistance by reference to the value $R_{seal1}$ and $R_{seal2}$. Similarly, the capacitance and conductance of the cell membrane which is disposed over passivation layer 24, $C_S$ and $G_S$, respectively, are distributed with the seal resistance $R_{seal}$. FIG. 2B illustrates four components of these values, $C_{S1}$ and $G_{S1}$ and $C_{S2}$ and $G_{S2}$.

In the circuits represented in FIGS. 2A and 2B, the impedances of the microelectrode 20, $Z_{elect}$, and the reference electrode, $Z_{ref}$, can be determined in a variety of ways. These values, as well as the resistance of the solution, $R_{soln}$, can be factored out, for example, by normalizing to data obtained prior to introduction of the cells to the system. Thus, by measuring the total impedance across each microelectrode and the reference electrode, it is possible to resolve impedances or changes in impedance relating to the cell motility, adhesion to the cell substrate (based on $R_{seal}$), and changes in cellular membrane capacitance and conductance. It is further possible to monitor the activity of cellular ion channels and the action potential parameters of the cell as a result of their effects on the impedance measured between each microelectrode and the reference electrode.

It is noted that the particular electrical characteristics of the cell, such as the capacitance and the conductance of the cellular membrane, are determined from the measured impedance by modeling the cell in accordance with known techniques. Various cell models may be used. For example, the cell can be modeled as a flat, circular "pancake" (i.e., as a disk). Other models may include a square or rectangular "pancake", a sphere, a cube, or a rectangular box.

FIG. 3 illustrates an embodiment of the invention in which a homodyne detection technique is used to detect the signals resulting from the application of a signal voltage between each microelectrode and the reference electrode. A quadrature synthesizer is used to generate both sine and cosine signals of a programmed frequency and amplitude. The sine voltage signal is attenuated as needed and selectively applied to individual microelectrodes. The resulting signal is detected by a transimpedance stage which holds the large reference electrode at a reference potential (in this case, ground) via negative feedback. Automatic gain control is used to amplify the voltage output of the transimpedance stage. The amplified signal is multiplied in quadrature by the source signals and is low pass filtered to provide the real and imaginary components of the measurement. Quadrature multiplication allows for signal detection, for example, at the excitation frequency with high noise immunity. Known resistance values are used to calibrate the system for electrode impedance measurements.

In the embodiment shown in FIG. 3, a quadrature synthesizer 30 generates both a sine wave and cosine wave, $A\sin(\omega t)$ and $A\cos(\omega t)$. In this particular example, the generated signals have a frequency of 1 kHz and an amplitude of 10 V peak to peak (P-P). Of course, it will be understood that the present invention is not limited to these particular values. For example, a system has been constructed capable of applying a signal of 100 Hz to 100 kHz.

The sine wave is attenuated 32, in this example, in a range from 0 to −80 dB. The attenuated signal is then selectively applied to particular microelectrodes 34. In this example, an analog multiplexer 33 is used to apply the attenuated voltage signal to each of an array of thirty-six microelectrodes. Again, the invention is not limited to the number of microelectrodes in the array or to the components used for selective application of the signal to each of the microelectrodes.

The resulting current is detected by a transimpedance amplifier 35 which maintains the large reference electrode 31 at a virtual ground potential. The transimpedance amplifier outputs a signal, $B\sin(\omega t+\phi)$. In this example, a known resistance $R_{sense}$, 36, is applied across the input and output of the transimpedance amplifier. Thus, the amplitude B of the signal is described by the following:

$$B = A' R_{sense}/|Z_{UNKNOWN}|$$

where A' is the amplitude of the attenuated applied voltage signal and $Z_{UNKNOWN}$ is the unknown impedance across the microelectrode 34 and large reference electrode 31.

The signal from the transimpedance amplifier is then amplified by an automatic gain control (AGC) amplifier having a variable gain $A_V$. In the particular example shown in FIG. 3, the signal is amplified in a range between 0 and 120 dB. The resulting signal, $A_V B\sin(\omega t+\phi)$, is multiplied in quadrature with mixers 38a and 38b and then low pass filtered to obtain real and imaginary components X and Y.

Thus, the signal from AGC amplifier 37 is mixed with the signal $A\sin(\omega t)$ to obtain the following signal:

$$(A_V AB/2)[\cos \phi - \cos (2\omega t+\phi)]$$

The signal from the AGC amplifier is also mixed with the signal $A\cos(\omega t)$ to obtain the following signal:

$$(A_V AB/2)[\sin \phi + \sin (2\omega t+\phi)]$$

Thus, when low pass filtered, the following components remain:

$$X = (A_V AB \cos \phi)/2$$

and $$Y = (A_V AB \sin \phi)/2$$

In one example, the system is calibrated with a known value resistance to obtain calibration values $X_{CAL}$ and $Y_{CAL}$. The magnitude $|CAL|$ and phase $\phi_{CAL}$ of the calibration values are then determined as follows:

$$\phi_{CAL} = \arctan [Y_{CAL}/X_{CAL}]$$

$$|CAL| = [X_{CAL}^2 + Y_{CAL}^2]^{1/2}$$

Once the calibration values are obtained, measurements are taken with the microelectrodes and measurement values $X_{MEAS}$ and $Y_{MEAS}$ are calculated as indicated above. Based on these values, the phase and magnitude for the respective measurements, $\phi_{MEAS}$ and |MEAS| are calculated as follow:

$$\phi_{MEAS} = \arctan[X_{MEAS}/Y_{MEAS}]$$

$$|MEAS| = [X_{MEAS}^2 + Y_{MEAS}^2]^{1/2}$$

Given the respective values for $X_{CAL}$, $Y_{CAL}$, $X_{MEAS}$ and $Y_{MEAS}$, one can divide the magnitude of the measured value |MEAS| by the magnitude of the calibration value |CAL| and then solve for the magnitude of the unknown impedance $|Z_{UNKNOWN}|$. The phase of the unknown impedance $Z_{UNKNOWN}$ is determined as follows:

$$\phi_Z = \phi_{MEAS} - \phi_{CAL}$$

In the example shown in FIG. 3, the detected values for X and Y are sampled with an analog to digital converter installed in a PC.

An alternate embodiment of the invention is illustrated in FIG. 10. In this example, a signal monitoring and processing means 104 such as a PC, receives the detected signal through an analog/digital converter at a sample rate sufficient to read the detected sinusoidal signal. For example, the output from the AGC amplifier of FIG. 3 could be A/D converted and input to a PC. The signal monitoring and processing means 104 obtains phase and magnitude values from the unknown impedance after directly converting the respective sinusoidal output for extraction of data. In this example, the signal monitoring and processing means 104 provides the capability of performing a spectral analysis to monitor, in real time, characteristics such as changes in cell action potential parameters and cell impedance. By performing real time Fourier analysis, it is possible to monitor distortion caused by nonlinear electrode effects. Thus, it is a feature of the invention that the system may perform spectral analysis of the resulting signals in order to monitor changes in various characteristics in real time.

As described generally above, data obtained with the embodiment shown in FIG. 3 can be "normalized" to various conditions in order to monitor the characteristics of cells which adhere to the respective microelectrodes 34. For example, the membrane capacitance and conductance of individual cells which adhere to the microelectrodes can be monitored, based on various models of the cells. Various other techniques are described herein.

The embodiment of FIG. 3 provides high sensitivity and signal resolution for a large range of applications. One characteristic of the embodiment of FIG. 3 is that the low pass filters have a characteristic settling time. Where several electrodes are monitored sequentially, this characteristic may introduce a minor delay. It is possible to provide an even faster measurement cycle by heterodyning the detected signal to a higher frequency and then bandpass filtering to obtain phase and magnitude information. Such a technique permits real time observation of extremely rapid variations in electrical characteristics of the cell, such as variations in transmembrane impedance (caused by opening and closing of ion channels).

FIG. 4 illustrates an embodiment of the invention in which a heterodyne detection technique is used. In this example, the same elements shown in FIG. 3 are referred to with identical reference numbers.

A test signal oscillator 40 generates sine and cosine signals, $A\sin(\omega_{test}t)$ and $A\cos(\omega_{test}t)$ at a frequency $\omega_{test}$. As in the embodiment of FIG. 3, the voltage sine signal is selectively applied across each microelectrode 34 and the reference electrode 31. The resulting current is detected using transimpedance amplifier 35 and AGC amplifier 37. Mixers 42a and 42b multiply the resulting signal $B\sin(\omega_{test}t+\phi)$ in quadrature by sine and cosine signals generated by a local oscillator 41. The signals produced by the local oscillator have an angular frequency $\omega_{LO}$, which is the sum of the test frequency $\omega_{test}$ and an intermediate frequency $\omega_{IF}$. As indicated in FIG. 4, the respective outputs of mixers 42a and 42b are represented, respectively, by:

$$(AB/2)\cos[\omega_{IF}t+\phi] - (AB/2)\cos[(2\omega_{test}+\omega_{IF})t+\phi]$$

$$(AB/2)\sin[\omega_{IF}t+\phi] + (AB/2)\sin[(2\omega_{test}+\omega_{IF})t+\phi]$$

These outputs are bandpass filtered at the intermediate frequency $\omega_{IF}$ and the filtered output detected using amplitude modulation detectors 46a and 46b to provide real and imaginary components $X=|(AB\cos\phi)/2|$ and $Y=|(AB\sin\phi)/2|$. The algebraic sign of X and Y must be determined by a phase-sensitive detector (not shown in FIG. 4), as is well known in the art. The unknown impedance between the microelectrode and the large reference electrode is then calculated in the manner described above.

It will be appreciated that in addition to the exemplary embodiments discussed above, various other alternative embodiments are possible for impedance measurement. For example, measurement in the time domain can be used rather than homodyning to extract phase and magnitude information about each impedance. This may be accomplished, for example, by using a step function in place of the above-mentioned sinusoidal signal to drive each microelectrode. Further, the frequency of excitation and the sinusoidal input signal amplitude can be expanded beyond the exemplary ranges identified above.

FIG. 5 is a cross-sectional view of a portion of a monolithic structure containing a microelectrode array according to the present invention. An insulating layer 55 is formed over an underlying substrate 54. An electrically conductive interconnect trace pattern 52 is deposited using a conventional thin-film deposition technique (e.g., sputtering). A passivation layer 58 (e.g., silicon nitride) is formed over the interconnect trace pattern. Portions of the passivation layer 58 are etched to form vias that expose portions of the interconnect 52 so as to define planar microelectrode surfaces. In the particular embodiment shown in FIG. 5, the monolithic structure includes an integrated photosensor 57, for example, a photodiode or CCD. This component is disposed underneath the insulating layer 55, which, in this example, is transparent.

It is a feature of the invention that the microelectrode array may be formed in a device which advantageously integrates various other components. An exemplary integrated device 60 is now described in reference to FIG. 6.

In the embodiment shown in FIG. 6, an etched cavity 65 (not to scale) is formed in a substrate 66. The etched cavity 65 provides a gap which isolates the components of the integrated device 60 from its packaging (not shown), thereby functioning as a thermal isolation membrane. Formed on the substrate is an insulation layer 69 which electrically isolates a microelectrode array 68, such as that described above, from the substrate 66.

Between the substrate 66 and the microelectrode is an optional thin film heater 64. The thin film heater 64 is thermally coupled to, yet electrically insulated from the microelectrode array 68 which is disposed over the heater 64 in this example. The thin film heater 64 is used to maintain the microelectrode array (and the electrolyte) at a substantially constant temperature (typically 37° C.). The thin film heater may be manufactured according to standard techniques known in the art, and provide more energy efficiency compared to non-integrated heaters.

The example shown in FIG. 6 illustrates other optional features of the invention. Specifically, the integrated device 60 includes various sensors 62 which may be utilized alone or in combination with each other. For example, the sensors 62 may include a pH sensor and/or a temperature sensor. As known in the art, the pH sensor can be constructed by deposition of a metal electrode (such as an iridium electrode) whose electrical potential varies with changes in pH. The inclusion of an integrated pH sensor not only provides for monitoring of pH sensors caused by external factors, but also permits monitoring of pH changes caused by the cells which adhere to the integrated structure 60.

Additionally, the integrated temperature sensor referred to above may advantageously provide closed loop temperature control, particularly when used in conjunction with the integrated heater 64. As with the other elements described above, the temperature sensor can be fabricated conveniently in accordance with standard microfabrication techniques. For example, layers of different metals may be deposited to form a thermocouple junction or the TCR of the thin film heater could be used directly to monitor temperature. The output from this sensor could then be used via suitable external (or on-chip) circuits to selectively activate the thin film heater 64. Alternatively, it could be used to selectively activate non-integrated heating elements.

Again, various modifications and alternative embodiments will be apparent to those skilled in the art without departing from the invention. For example, the microelectrodes and their respective interconnects and bond pads may comprise any biocompatible conductive substance, such as iridium, activated iridium, gold, platinum, polysilicon, aluminum, ITO, or TiW, bare or electroplated with platinum black.

Additionally, the substrate 66 of the integrated device may comprise a variety of materials, such as silicon, glass, metal, quartz, plastic, ceramic, polyethylene, or any other suitable type of polymer. It is noted that glass substrates have been found to provide reduced parasitic capacitance.

Other variations of the structure which are not essential to the underlying features of the invention include changes in the composition of the passivation layer. For example, devices made in accordance with the invention have utilized different passivation layers ranging from 1 to 5 $\mu$m in thickness. The passivation layer may comprise any suitable material, including low stress PECVD silicon nitride, silicon carbide, TEFLON™, polyimide, ceramic, photoresist, or any type of polymer or thermal plastic, or combination thereof.

Furthermore, the monolithic structures which include the microelectrode array may be packaged in various configurations. According to one example, arrays are fabricated on structures which are divided into individual 9×9 mm chips. The chips are packaged in a standard 40-pin ceramic dual in-line package, or any other types of package which contains a suitable number of leads. In this example, the bondwires are encapsulated (for mechanical and electrical robustness) in a nontoxic low stress epoxy. Bondwire encapsulation may also be achieved with polyurethane, polyethylene, wax, silicon carbide, silicon nitride, TEFLON™, or polyimide.

Of course this construction may be modified in many different ways. For example, instead of dicing the arrays into multiple chips, the arrays can remain on the same substrate to form multiwell plates, each containing an array of electrodes. In such a configuration, Petri dishes are bonded to the substrate to define respective wells. The Petri dishes can comprise polystyrene, glass, polyethylene, TEFLON™, metal, or any other type of polymer. The Petri dishes may be bound to a chip formed in accordance with the invention using conventional materials and techniques, such as epoxy, polyurethane, wax, or thermoplastic, using thermal or ultrasonic processes. In this alternate construction, bondwire connections can be eliminated by use of a substrate configured to mate directly with a connector, such as an edge card connector or pads for a standard pin type connector. Of course, this would require the substrate area to be significantly larger than the active electrode area.

The membrane capacitance, membrane conductance, cell/substrate separation and action potential parameters of a cell are significant markers regarding a cell's metabolic state, including general cellular health and ionic channel activity. The membrane potential, the voltage difference across a cell's plasma membrane, depends on the distribution of ionic charge. Generally, the distribution of ionic charge determines the electric potential, or voltage. For example, in a metallic conductor, the mobile particles carrying charge are electrons; in an aqueous solution, the mobile particles are ions such as $Na^+$, $K^+$, $Cl^-$, and $Ca^{+2}$. In an aqueous solution, the number of positive and negative charges are normally balanced exactly, so that the net charge per unit volume is zero. An unbalanced excess of positive charges creates a region of high electrical potential, repelling other positive charges and attracting negative charges. An excess of negative charges repels other negative charges and attracts positive charge. When an accumulation of positive charges on one side of a membrane is balanced by an equal and opposite accumulation of negative charges on the other side of the membrane, a difference of electrical potential is set up between the two sides of the membrane.

Charge is carried back and forth across the cell membrane by small inorganic ions—chiefly $Na^+$, $K^+$, $Cl^-$, and $Ca^{+2}$—but these can traverse the lipid bilayer only by passing through special ion channels. When the ion channels open, the charge distribution shifts and the membrane potential changes. Of these ion channels, those whose permeability is regulated are the most significant; these are referred to as gated channels. Two classes of gated channels are of crucial importance: (1) voltage-gated channels, especially voltage-gated $Na^+$ channels, which play the key role in the rapid changes in electrical energy by which an action potential is propagated along a nerve cell process; and (2) ligand-gated channels, which convert extracellular chemical signals into electrical signals, which play a central role in the operation of synapses. These two types of channels are not peculiar to neurons: they are also found in many other types of cells.

The present invention permits detection and monitoring of characteristics of a cell. As noted at the outset, these characteristics include cell impedance (cell membrane capacitance and conductance), action potential parameters, cell membrane capacitance, cell membrane conductance, and cell/substrate seal resistance. These electrical characteristics, in turn, correlate well with the metabolic state of the cell. The present invention, thus, provides an apparatus and method for monitoring cells and for monitoring the impact that an analyte will have upon the metabolism of a cell. It is to be appreciated that such analytes include pharmaceutical agents, drugs, environmental factors, toxins, chemical agents, biological agents, viruses, and cellular adhesion promoters. Thus, the present invention is useful in screening and assaying broad classes of materials for their impact on cellular metabolism.

Other features of the invention will become apparent in the course of the following descriptions of exemplary embodiments which are given for illustration of the invention and are not intended to be limiting thereof.

EXAMPLES

A 6×6 array of 10 μm diameter planar microelectrodes (100 μm pitch) was fabricated. In the array, a 500 nm thermal silicon dioxide layer electrically isolated the microelectrodes from the underlying silicon substrate. Although the substrate in this example is silicon, any other suitable substrate material may be employed, including, but not limited to, glass, metal, quartz, plastic, ceramic, and polyethylene.

In this example, the microelectrodes were constructed of iridium and these microelectrodes, as well as the gold interconnects and bondpads, were deposited utilizing lift-off techniques, followed by deposition of a 1 μm low stress PECVD silicon nitride passivation layer. However, the microelectrodes do not necessarily have to be constructed of iridium; any suitable electrode material is appropriate. For example, the electrodes could be constructed of gold, platinum, polysilicon, aluminum, ITO, TiW, or other suitably equivalent material. Amorphous "platinum black" may be electroplated onto the microelectrodes to lower their impedance. Moreover, the passivation layer can, alternatively, comprise silicon carbide, TEFLON™, polyimide, ceramic, or any type of polymer or thermal plastic. Vias were etched through the nitride layer to define the electrodes and bondpad openings.

In a preferred embodiment of the present invention, the microelectrodes can also provide a means for sensing the pH of the solution inside the cell culture chamber.

While, in this example, a 9×9 mm chip comprising the array was packaged in a standard 40-pin ceramic dual in-line package, it will be appreciated that other types of packages containing other number of leads may also be used. The bondwires were encapsulated for mechanical and electrical robustness in a nontoxic low stress epoxy. Bondwire encapsulation may also be achieved with polyurethane, polyethylene, wax, silicon carbide, silicon nitride, TEFLON™, or polyimide.

It will be appreciated that in an alternate configuration, a number of arrays could be assembled on a substrate, forming multiwell plates, each well containing an array of electrodes.

NG108-15 cells (neuroblastoma×glioma hybrid cells) were cultured on the microelectrode array in serum-containing media using standard cell culture protocols. For NG108-15 cells, a suitable protocol is described in V. C. Kowtha, et al., "Comparative Electrophysiological Properties of NG108-15 Cells in Serum-Containing and Serum-Free Media", *Neurosci Lett.*, 164, 129–33 (1993). These cells were chosen because they may be utilized for many types of morphological and biochemical studies; the NG108-15 cells express at least four major families of voltage-sensitive channels, including voltage-gated sodium channels, that respond to a variety of ion channel blockers. However, it is to be understood that many different types of cells are suitable as a component of the present invention. In a preferred embodiment, the cells are human cells; in another preferred embodiment of the present invention, the cells are simian or human totipotent primordial stem cells, capable of differentiating into many groups of differentiated cells. Such stem cells could be differentiated into a desired type of tissue (e.g., cardiac or hepatic or neurons). In such an embodiment, the cultured stem cells would be differentiated into those types of cells whose behavior and characteristics would be of interest.

The chips, cultured with cells, were placed in a $CO_2$ incubator (37° C., 10% $CO_2$) for 24 to 48 hours to ensure adequate adhesion to the microelectrodes. The chips were then removed from the incubator and placed into an impedance measurement system, similar to that illustrated in FIG. 3. The temperature of the substrate was regulated by an analog feedback loop using a cold-junction compensated thermocouple and a solid state Peltier device. Temperature regulation of the substrate of better than ±0.3° C. was achieved at 37° C. The temperature of the cell culture was also maintained at 37° C.

It will appreciated that, alternatively, a thin film integrated heater can be provided below the electrode array to heat directly the cultured array, or a separate thin film heater may be provided under the packaged chip. In such an embodiment, a thermally isolated membrane can be provided below the electrodes. While atmospheric $CO_2$ concentration was not controlled in this experiment, buffers in the culture medium adequately maintained the pH for the duration of the impedance measurements.

A 1 kHz, 100 m V P-P sinusoidal wave was applied to a single electrode in the array. This signal was small enough to ensure linear electrode characteristics. The resulting current flowing through the large reference electrode into a virtual ground was used to calculate the effective impedance of the cell/electrode interface combination. Electrode impedance was monitored across the array at approximately three minute intervals.

A quadrature synthesizer was used to generate both sine and cosine signals of programmed frequency and amplitude. The 10V P-P sinewave signal was attenuated as needed (e.g., from 0 dB to −80 dB) and connected to each individual electrode of the array via an analog multiplexer. The resulting current was monitored across a 100 Hz to 100 kHz frequency range with sinusoidal excitation voltages from 1 mV to 100 mV P-P by a transimpedance stage which holds the large reference electrode disposed at virtual ground. Automatic gain control (0 dB to 100 dB) was used to amplify the voltage output of the transimpedance stage. Of course, it will be appreciated that the frequency of excitation and the sinusoidal input signal amplitude can be expanded beyond the above-noted ranges.

This amplified signal was multiplied in quadrature by the source signal and low pass filtered (fourth order Butterworth at 10 Hz) to provide the real and imaginary components of the measurement. Quadrature multiplication (a common lock-in amplifier technique) allowed for signal detection (at the excitation frequency) with high noise immunity.

It will be appreciated that the impedance measurement system can be modified in a variety of ways. For example, time domain measurements could be used rather than homodyning to extract phase and magnitude information about each impedance. This may be accomplished by using a step function in place of the above-mentioned sinusoidal signal to drive each electrode. Further, the output signals could be read directly into a computer (after A/D conversion) for real time Fourier analysis in order to determine distortion caused by nonlinear electrode effects. Similarly, by eliminating the analog mixers and the filtering, the sinusoidal outputs could be directly converted to digital format to provide computerized extraction of data. This embodiment replaces the mixers and filters shown on the output side of the AGC amplifier 37 of FIGS. 3 and 4 with digital signal processing means, known in the art.

Additionally, instead of homodyning and then extracting DC information, it is possible to heterodyne to a higher frequency and then bandpass to extract magnitude and phase information. Such an approach would allow for faster measurements (in contrast to the present embodiment where time is determined by settling of LPF), and permit simultaneous measurement of impedance and action potentials or measurement of action potentials by impedance means. This approach would allow observation of the opening and closing of ion channels with electrically active cells by monitoring the cell's transmembrane impedance in real time.

Another feature of the invention provides for simultaneous observation of action potentials and impedances using the same microelectrode array. For example, FIG. 11 shows an embodiment in which action potential measurements may be made in accordance with conventional techniques by passively monitoring each microelectrode in array 8. Typically this is accomplished by detecting the signal from the microelectrode (via a buffer), amplifying the signal (current or voltage) and measuring the action potential. As indicated at reference 112, it is also possible to perform a spectral analysis of the action potential. Upon activation of switch 115, the microelectrodes are driven with a signal 10 in accordance with the techniques described above. Thus, by switching between the two systems at a sufficiently high rate, substantially simultaneous measurement and recording of action potentials and impedances may be achieved. It will be appreciated that although two separate signal processing paths are shown in FIG. 11 for purposes of illustration, in practice, the signal monitoring and processing means 112 and 114 may utilize the same hardware (such as a PC), for example, on a time sharing basis.

The culture media was exchanged for new media with the same formulation in order to "normalize" the solution pH for subsequent addition of analytes. This step was used to address any significant pH changes which might occur during the 24 to 48 hour culture period, resulting from cell metabolic processes. Culture media containing the analyte to be tested were exchanged for the existing media and the resulting impedance changes was monitored over time. After a leveling of impedance response, the test solution was rinsed twice and replenished with new cell culture media. Again, the resulting impedance was monitored. Finally, the cells were rinsed an additional time to ensure full removal of any remaining test solution.

Impedance measurements across the array allow for determination of cell position and coupling to electrodes when the measurements are normalized to data taken prior to cell plating. Where detection of environmental factors or other external stimuli is desired, the impedances are normalized to the first measurement of a series.

System performance and variability were evaluated by measuring a 1 MΩ, 1% metal film resistor in place of the electrode array (measured electrode impedances at 1 kHz typically ranged from 10 kΩ to 2 MΩ, depending on cell coupling). With twenty trials, maximum single channel variations of 0.11% and channel-to-channel variations of 0.12% in impedance magnitude were observed. This is indicative of the anticipated measurement noise due to the electronics.

Impedance measurements normalized to the bare chip impedances were used to directly correlate cell placement over electrodes. FIGS. 7A and 7B presents impedance data for healthy cells growing on the electrode array. FIG. 7A is an optical photograph of cells growing on an electrode array. FIG. 7B is a two-dimensional impedance magnitude map (with magnitude represented by shading) normalized to the bare chip impedance. Boxes in FIG. 7A indicate electrodes with apparent tight cell/electrode coupling as shown in the impedance map of FIG. 7B. Interpolation was used to form contours between discrete data points.

As FIGS. 7A and 7B make apparent, regions with cells positioned directly over an electrode (highlighted with boxes in the optical image) correspond to regions of high impedance. Where action potential signals are to be measured using passive monitoring of the extracellular voltage from the cultured cells, tight cell/electrode coupling is desired for improved signal-to-noise ratio (SNR). Thus, the impedance monitoring of the present invention may be used to determine which electrodes are covered by tightly coupled cells and should be monitored for action potential signals or impedance measurements.

Figure 8A:
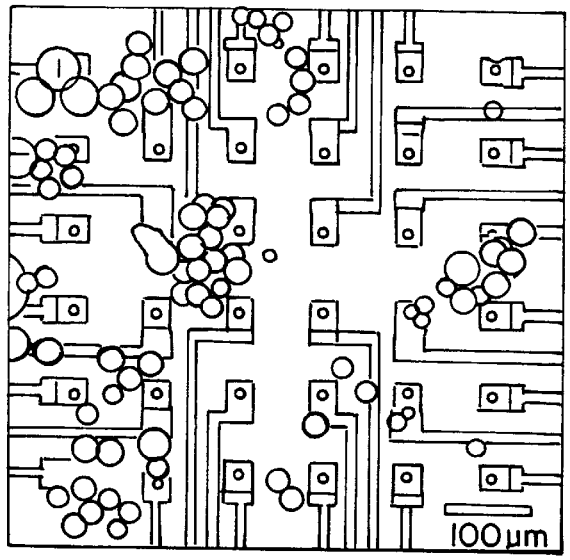
FIG. 8A is a diagramatic represention of an optical photograph of NG108-15 cells on an electrode array following lysing in a hyperosmolar solution for five minutes, in accordance with an example of the invention.

Lysing (causing cellular death by generation of significantly different osmolality inside and outside of the cell, resulting in rupture of the cellular membrane) the cells by perfusion with a hyperosmolar solution resulted in the data presented in FIGS. 8A and 8B. FIG. 8A is an optical photograph of NG108-15 cells following lysing in a hyperosmolar solution for five minutes. FIG. 8B is a two-dimensional image magnitude map normalized to the bare chip impedance.

FIGS. 8A and 8B reveal a clear decrease in measured impedance across the array. This decrease corresponds to a lifting of cells and partial removal of absorbed biological substances from the electrodes. These results illustrate the sensitivity of the impedance measurements to absorbed materials.

Figure 9A:
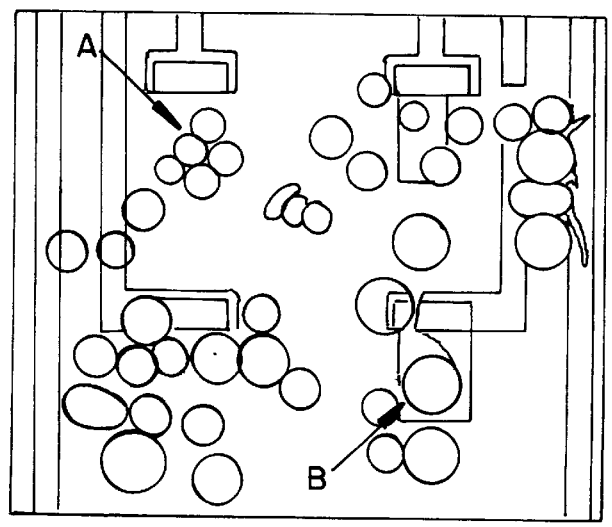
FIG. 9A is a diagramatic represention of an optical image of cells NG108-15 plated over several representative electrodes, in accordance with an example of the present invention.

To examine the effects of specific ion channel blockage, single electrode impedances were monitored over time as the highly specific blocker of voltage gated $Na^+$ channels tetrodotoxin (TTX) was added. An optical image of several representative electrodes is shown in FIG. 9A. The normalized impedance magnitude of electrodes A, B, and Control 1 of FIG. 9A as measured over three minute intervals is shown in FIG. 9B.

The addition of the sodium channel blocker tetrodotoxin (TTX) resulted in qualitatively different responses from different electrode/cell combinations. The most pronounced effects may be seen with trace A in FIG. 9B. With the addition of TTX, the cell clump over electrode A in FIG. 9A responded with a dramatic increase (180%) in measured impedance magnitude, most likely corresponding to blockage of voltage-gated $Na^+$ channels. As these channels are blocked, the resulting impedance is believed to increase due to decreased resistive conductance through them. This particular clumped cell response did not recover upon removal of the TTX solution.

It will be appreciated that the experimental results obtained with the TTX assay demonstrates the utility of the present invention as a tool for pharmaceutical and toxin screening. Specifically, in place of TTX any analyte may be assayed for the effect or impact that addition of the analyte to the cell culture medium will have upon the electrical characteristics of the cell. As noted elsewhere in the specification, the analyte can be one or more materials selected from the group consisting of pharmaceutical agent, drug, environmental factor, toxin, chemical agent, biological agent, and virus. In addition, the present invention includes a method of monitoring the effect of an analyte in vitro, which in analogy to the TTX experiment, comprises the steps of providing in a cell culture chamber a monolithic device that includes an array of planar microelectrodes disposed on a substrate, the array of microelectrodes being connected to a conductive pattern having contacts points connected thereto; culturing cells in a medium provided within the cell culture chamber, wherein the diameter of a cell is larger than the diameter of a microelectrode; incubating the cells for a time sufficient to ensure adhesion to the microelectrodes; selectively applying an electrical signal between each microelectrode and a reference electrode disposed within the medium; detecting signals resulting from the application of the electrical signal between the microelectrodes and the reference electrode; determining characteristics of individual cells which adhere to the respective surfaces of the microelectrodes, the characteristics being selected from the group consisting of impedance, action potential parameters, cell membrane capacitance, cell membrane conductance, and cell/substrate seal resistance; introducing the analyte into the medium; repeating the step of determining; and comparing the characteristics both prior to and subsequent to introducing the analyte and monitoring the effect of the analyte on the cells which adhere to the microelectrodes.

In addition, it will be appreciated that, in analogy to the pharmaceutical and toxin assay described herein, the present invention may also be employed to measure the degree to which culture cells adhere to the respective surfaces of particular microelectrodes and to assay the effectiveness of a cellular adhesion promoter, by means of detecting and monitoring the impedance of individual cells, and changes therein.

A system has been presented that monitors cellular viability and position by impedance measurement, demonstrating potential use in a variety of sensors. Maps of electrode impedance have been shown to correlate directly to cell positioning over an electrode array. The results presented indicate significant cellular response as compared to control electrodes without cells. The effective use of electrodes small enough (10 $\mu$m diameter) to study single cell/electrode coupling has been demonstrated. Investigations of this and other agents along with tight control (and purposeful variation) of environmental factors utilizing this system's full capabilities (frequency variation and signal source amplitude variation) should allow for development of detailed models of cell/electrode coupling and the mechanisms affecting cell membrane impedance.

By utilizing different cell types, it is possible to tune the sensitivity of the sensor to specific applications. It is to be appreciated that any anchorage-dependent cell type, derived from any organism is suitable in the present invention. Non-electrically-active cell types, such as hepatic cells, could be used for toxin detection. For sensors utilizing electrically active cells, impedance measurement may be used to determine which electrodes are covered by cells (and therefore should be monitored), and as a secondary monitor of cellular viability. Possible application areas include: toxin detection, cell cytotoxicity testing, pharmaceutical screening, and environmental monitoring.

In addition to the variations noted above, the system according to the invention could be modified to provide alternate impedance and action potential recording. Similarly, action potential parameters can be recorded, based on electrical stimulation with the electrodes and subsequent action potential or impedance recording.

Alternatively, an optical sensor could be incorporated into the system to detect fluorescence of engineered cells. An integral or external optical sensor could be utilized to detect fluorescence in conjunction with impedance and/or action potential measurements. It could also be used to detect voltage-sensitive dyes in conjunction with impedance and/or action potential measurements.

Real-time spectral analysis (Fourier) of action potentials and/or impedance could be used for hybrid biosensors in toxin detection and pharmaceutical screening. In this regard, changes in the spectrum can be related to specific channel activation and different toxin/pharmaceutical effects. Thus, there are possibilities for fast, real-time determination of changes in impedance and action potential shape.

In addition to the features described above, the invention may be adapted for use in quality control testing of microelectrode arrays, such as those adapted for use in wet electrochemical systems. In such an embodiment, a test voltage signal is applied across each microelectrode. The resulting signal is detected in accordance with the signal monitoring and detection techniques described generally in reference to FIG. 1 and more specifically in reference to the embodiments of FIGS. 3 and 4. As described above, these techniques permit convenient measurement of both phase and magnitude of an unknown impedance.

It will be appreciated that these techniques permit testing of microelectrode impedance in an efficient manner. For example, a newly fabricated microelectrode array may be tested in both wet and dry states using a spectrum of test signal frequencies in order to measure the impedance of each microelectrode in absolute terms. By testing with different frequencies, a complete measurement of each microelectrode's capacitance and resistance can be determined and compared with a desired tolerance. Additionally, the relative impedance of each microelectrode with respect to each other may also be determined.

Yet another feature of this technique is its application for testing the characteristic impedances (in either absolute or relative terms) of each microelectrode in an array before and after introduction of the array into a wet electrochemical system. For example, the absolute or relative impedances of the microelectrodes could be measured first in a "dry" state (i.e., prior to use in an wet electrochemical system). The test array is then placed in a wet electrochemical system, such as generally illustrated in FIG. 1, and then impedances could be measured in the "dry" system, for example, using a reference electrode having known impedance characteristics. In this way, the "wet" data may be normalized against the data of the dry system, thereby permitting, for example, calculation of parasitic effects characteristic of the "dry" system which then may be taken into account while using the microelectrode array. Of course, this technique could be utilized in a variety of applications. In addition to testing microelectrode arrays designed for detection of cellular electrical characteristics (such as the embodiments described in reference to FIGS. 5 and 6), the above described technique could be used for efficient quality control testing of any electrode array, regardless of the intended use of the array.

Preferred embodiments of the invention have now been described in fulfillment of the above-mentioned objects of the invention. Many other modifications, alternatives, and variations will be apparent to those skilled in the art without departing from the spirit and scope of the invention. It is intended that the invention encompass all such modifications and improvements and be limited in scope only with respect to the claims appended hereto.

What is claimed is:

1. An apparatus comprising:
a monolithic device including an array of planar microelectrodes disposed on a substrate, the array of microelectrodes being connected to a conductive pattern having contact points connected thereto;
a cell culture chamber in which the integrated device is disposed, the cell culture chamber being configured to contain a medium for cultured cells in a volume surrounding the respective surfaces of the microelectrodes, wherein cells are introduced into the cell culture chambers and a portion of the cells adhere to respective surfaces of the microelectrodes,
wherein the diameter of a cell is larger than the diameter of a microelectrode;
a reference electrode disposed within the cell culture chamber;
means electrically connected to the contact points connected to the array of microelectrodes for selectively applying an electrical signal between each of the microelectrodes and the reference electrode;
means for detecting signals resulting from the application of the signal between each of the microelectrodes and the reference electrode;
a phase detector electrically connected to the signal detecting means; and
means for monitoring characteristics of cells which adhere to the respective surfaces of the microelectrodes based on impedance values derived from the resulting signals, the characteristics being selected from the group consisting of impedance, action potential parameters, cell membrane capacitance, cell membrane conductance, and cell/substrate seal resistance.

2. The apparatus according to claim 1, wherein the respective diameters of the microelectrodes are less than or equal to one half the diameter of a cell adhered thereto.

3. The apparatus according to claim 1, wherein the respective diameters of the microelectrodes are between about 4 and 20 $\mu$m.

4. The apparatus according to claim 1, wherein the monolithic device includes an integrated sensor which provides an electrical signal indicative of the pH of the medium.

5. The apparatus according to claim 1, wherein the monolithic device includes a heating means formed integrally therein.

6. The apparatus according to claim 5, wherein the monolithic device further includes a thermal isolation membrane.

7. The apparatus according to claim 5, wherein the heating means comprises an integrated thin film heater.

8. The apparatus according to claim 1, wherein the monolithic device further includes an integrated temperature sensor, the temperature sensor providing an electrical signal used to selectively activate a heater means, the heater means maintaining a substantially constant temperature.

9. The apparatus according to claim 1, wherein the monolithic device further includes an integrated optical sensor.

10. The apparatus according to claim 1, wherein the characteristics comprise action potential parameters.

11. The apparatus according to claim 1, wherein the characteristics comprise impedance.

12. The apparatus according to claim 1, wherein the characteristics comprise impedance and action potential parameters.

13. The apparatus according to claim 1, wherein the characteristics comprise cell membrane capacitance.

14. The apparatus according to claim 1, wherein the characteristics comprise cell membrane conductance.

15. The apparatus according to claim 1, wherein the characteristics comprise cell/substrate seal resistance.

16. The apparatus according to claim 1, further including means for measuring action potential of cells adhered to the surface of the microelectrodes, wherein the impedance is determined substantially simultaneously with measuring action potential.

17. The apparatus according to claim 1, wherein the cells include cells differentiated from primordial stem cells.

18. The apparatus according to claim 1, wherein the means for monitoring detects activation of voltage-gated ion channels of the cells adhering to microelectrodes on the basis of the characteristics.

19. The apparatus according to claim 1, wherein the means for monitoring detects changes in characteristics associated with the introduction of an analyte into the medium.

20. The apparatus according to claim 19, wherein the analyte is at least one material selected from the group consisting of pharmaceutical agent, drug, environmental factor, toxin, chemical agent, biological agent, and virus.

21. The apparatus according to claim 15, wherein the means for monitoring detects the degree to which the individual cells adhere to the respective surfaces of particular microelectrodes on the basis of cell/substrate seal resistance.

22. The apparatus according to claim 1, wherein the means for selectively applying an electrical signal includes a multiplexer for selectively applying a signal to each of the microelectrodes.

23. The apparatus according to claim 1, wherein the detecting means includes means for homodyne detection of the resulting signal.

24. The apparatus according to claim 23, wherein the detecting means includes means for multiplying the resulting signals in quadrature with the applied signal and low pass filtering the product to obtain real and imaginary components which are processed by the monitoring means.

25. The apparatus according to claim 1, wherein the characteristics are monitored as the applied electrical signal is varied at each microelectrode across different frequencies.

26. The apparatus according to claim 1, wherein the characteristics are monitored as the applied electrical signal is varied at each microelectrode across different excitation voltages.

27. The apparatus according to claim 1, wherein the means for detecting includes means for heterodyne detection of the resulting signal.

28. The apparatus according to claim 27, wherein the means for heterodyne detection include: a local oscillator which produces a signal having a frequency based on the frequency of the applied signal and an intermediate frequency, means for multiplying the resulting signal in quadrature by the signal from the local oscillator, and a bandpass filter tuned to the intermediate frequency to filter the product thereof to obtain real and imaginary components of the resulting signal.

29. The apparatus according to claim 1, wherein the means for monitoring includes means for performing spectral analysis of the resulting signal, whereby changes in the characteristics are monitored in real time.

30. An apparatus comprising:
a monolithic device that includes an array of planar microelectrodes disposed on a substrate, the array of microelectrodes being connected to a conductive pattern having contacts points connected thereto;

a cell culture chamber in which the monolithic device is disposed, the cell culture chamber being configured to contain a medium for cultured cells in a volume surrounding the respective surfaces of the microelectrodes, wherein cells are introduced into the cell culture chamber and a portion of the cells adhere to respective surfaces of the microelectrodes, wherein the diameter of a cell is larger than the diameter of a microelectrode;

a reference electrode disposed within the cell culture chamber;

means for selectively applying an electrical signal between each microelectrode and the reference electrode;

means for detecting signals resulting from the application of the signal between the microelectrodes and the reference electrode;

means for processing the detected signals across a spectrum of frequencies to calculate the impedance spectrum of each microelectrode.

* * * * *